United States Patent
Anderson et al.

(10) Patent No.: US 6,436,127 B1
(45) Date of Patent: Aug. 20, 2002

(54) PHOTOTHERAPY METHODS AND SYSTEMS

(75) Inventors: Richard Rox Anderson, Lexington; Peter J. Dwyer, Franklin, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/169,083

(22) Filed: Oct. 8, 1998

Related U.S. Application Data (60) Provisional application No. 60/061,487, filed on Oct. 8, 1997.

(51) Int. Cl.[7] .............................................. A61B 9/01
(52) U.S. Cl. ........................ 607/89; 607/88; 600/317; 128/898
(58) Field of Search ................... 606/3, 4, 7, 10–19; 607/88–96; 600/310, 317; 604/19, 20; 128/898

(56) References Cited

U.S. PATENT DOCUMENTS

| | | | |
|---|---|---|---|
| 4,913,142 A | * | 4/1990 | Kittrell et al. ............. 606/7 |
| 5,300,097 A | | 4/1994 | Lerner et al. |
| 5,354,323 A | | 10/1994 | Whitebook |
| 5,456,260 A | | 10/1995 | Kollias et al. |
| 5,474,549 A | | 12/1995 | Ortiz et al. |
| 5,549,599 A | | 8/1996 | Sumiya |
| 5,556,612 A | | 9/1996 | Anderson et al. |
| 5,725,522 A | | 3/1998 | Sinofsky |
| 5,814,040 A | | 9/1998 | Nelson et al. |

FOREIGN PATENT DOCUMENTS

| | | |
|---|---|---|
| WO | WO93/03793 | 3/1993 |
| WO | WO93/21842 | 11/1993 |
| WO | WO97/15226 | 5/1997 |

OTHER PUBLICATIONS

Anderson, "Polarized Light Examination and Photography of the Skin," *Arch Dermatol*, 127:1000–1005, Jul. 1991.

* cited by examiner

*Primary Examiner*—David M. Shay
(74) *Attorney, Agent, or Firm*—Fish & Richardson P.C.

(57) ABSTRACT

The invention features methods and systems for treating inflammatory, proliferative skin disorders, such as psoriasis, with ultraviolet phototherapy. The methods and systems use optical techniques to scan a patient's skin, designate areas of affected skin, and selectively deliver high doses of phototherapeutic ultraviolet radiation to the designated areas. To insure that only affected areas of skin affected are designated for the high doses of UV radiation, the methods and systems use one or more optical diagnostics that relate to independent physiological features of affected skin.

20 Claims, 8 Drawing Sheets

PHOTOTHERAPY METHODS AND SYSTEMS

CROSS-REFERENCE TO RELATED APPLICATION

This application claims priority from provisional application No. 60/061,487, filed Oct. 8, 1997, the contents of which are incorporated herein by reference.

FIELD OF THE INVENTION

This invention relates to treatment of psoriasis and other proliferative skin disorders using phototherapeutic techniques.

BACKGROUND OF THE INVENTION

Psoriasis is a chronic, incurable, inflammatory skin condition affecting two to four percent of the world's population. Severity ranges from minor to life-threatening, and often fluctuates. Pathogenesis is unknown, but involves hereditary abnormalities of the immune system, with lymphocyte and neutrophil-mediated inflammation combined with hyperplasia of the epidermis. The epidermis proliferates at about ten times the normal rate. People with psoriasis literally leave a trail of skin flakes, and suffer from chronic itchy lesions, poor temperature regulation, fatigue from constant protein loss, and social stigma to the point of reclusion. There is an associated arthritis which attacks the fingers. The most common form is plaque-type psoriasis, in which well-demarcated lesions appear on the body, with normal skin between them. The plaques are red and scaly, quite different from the surrounding normal skin. The number of plaques ranges from several to several hundred, scattered over the trunk, arms, and legs. Psoriasis tends to spare the face, because ultraviolet (UV) light is therapeutic.

There is no cure for psoriasis. Drug treatments work by anti-inflammatory, antimitotic, hormonal, or immunosuppressive mechanisms. These include topical administration of corticosteroids, tar preparations, and vitamin D3 derivatives, systemic chemotherapy with methotrexate, and immunosuppression with cyclosporin A. Topical treatments are messy and expensive, but are still the main approach for patients with small areas of involvement. Corticosteroids tend to produce partial clearing followed by a "rebound" worse than the original disease severity, cause skin atrophy, and become progressively ineffective over time. Methotrexate is effective but causes liver toxicity. Cyclosporin A has multiple side effects, is expensive, and reserved for severe cases.

Ultraviolet phototherapy with or without photosensitizers, has been a mainstay of psoriasis treatment for many decades. UVB (290–320 nm) phototherapy is practical, effective, and often produces a long remission time after clearing, typically about five months. Psoralen, an extremely potent DNA-crosslinking photosensitizer, is also used orally or topically, followed by exposure to UVA radiation (320–400 nm). This is called Psoralen UVA (PUVA), a type of photochemotherapy. Phototherapy clears plaques in about 90% of patients, by combined mechanisms including apoptosis of keratinocytes, antimetabolic effects of DNA damage, and local and systemic immunosuppression. The patient stands in a "light box" lined with fluorescent lamps or other UV sources, and receives a prescribed fluence, i.e., a therapeutic dose of radiation. Each box is the size of a phone booth and costs about twenty to thirty thousand dollars. Since psoriasis does not usually affect the face, the patient typically wears a mask covering the face and eyes to prevent exposure to the therapeutic radiation. The rate of clearing is variable between patients, and depends on the exposure dose per treatment. An average of 20 to 30 treatments is needed for UVB (given 3 times per week) and an average of 15 to 25 treatments is needed for PUVA (given 2 times per week), depending on aggressiveness of the exposure dose protocol. Hence, it takes several months and many trips to the phototherapy center to clear psoriasis.

The "art" of phototherapy lies in achieving clearing without causing painful sunburn-like reactions. Thus, skin unaffected with psoriasis, i.e., normal skin, limits the therapeutic dose. The minimal erythema dose (MED) in normal skin is defined as the lowest fluence eliciting an inflammatory response, and is used to guide dosimetry. If the patient receives more than 1 MED, a "sunburn" will occur. At 3 MED a painful sunburn with blistering can occur, and at 10 MED a life-threatening burn results. Prior to a phototherapy treatment, the doctor determines the MED for a particular patient. As tanning develops during the course of multiple treatments, the UV fluence is increased, typically by 30 to 50 percent per treatment. At present, phototherapy consists of carefully but aggressively "pushing" the exposure dose based on response of the unaffected skin between plaques of psoriasis.

The cost of phototherapy, based on the number of trips and the clinicians' time, is estimated to be almost 1 billion dollars per year in the US. This does not include the cost of treating of skin cancers induced by phototherapy. In particular, prolonged exposure to UVB and PUVA cause basal cell carcinoma, squamous cell carcinoma, and melanoma. These diseases typically occur in areas of skin between plaques of psoriasis that have been exposed to large cumulative doses of UV radiation during phototherapy.

SUMMARY OF THE INVENTION

The invention features methods and systems for treating inflammatory, proliferative skin disorders, such as psoriasis, with ultraviolet phototherapy. The methods and systems use optical techniques to scan a patient's skin, designate areas of affected skin, and selectively deliver high doses of phototherapeutic ultraviolet radiation to the designated areas. The high dose levels are typically greater than two minimal erythema doses (MED) and often about ten MED. These dose levels are very effective at treating affected areas of skin, but would badly damage unaffected areas of skin, e.g., normal skin. To insure that only areas of skin affected by psoriasis or other disorders are designated for the high doses of UV radiation, the methods and systems use one or more optical diagnostics that relate to independent physiological features of affected skin.

The methods can be implemented by a system, e.g., a robotic system, that scans a patient's skin and constructs a digital map designating affected areas of skin based on one or more optical diagnostics. After a doctor or technician reviews, and possibly modifies, the digital map, the robotic system delivers the phototherapeutic radiation doses to the areas of skin designated by the map.

Alternatively, the automated designation of affected areas of skin and the selective delivery to the designated areas can be implemented with a manual device such as a fiber optic pen or comb. In such cases, a surgeon scans the patient's skin with the device to designate affected areas of skin. The treatment can be performed in real time based on the designation or, alternatively, the designation can be used to construct a digital map of the affected areas to guide subsequent treatment.

In general, the invention features a method for treating a proliferative skin disorder, e.g., psoriasis, in a patient by exposing the patient's skin to radiation; detecting at least one optical diagnostic signal in response to the radiation from a selected area of the patient's skin; determining from the optical diagnostic signal whether the selected area is affected by the skin disorder; and if the selected area is determined to be affected by the skin disorder, delivering an effective dose of phototherapeutic radiation to the selected area, e.g., using a laser, such as a xenon chloride excimer laser. The method can be automated. The selected area can be less than about 1 $cm^2$.

In specific embodiments, the phototherapeutic radiation is ultraviolet radiation having a wavelength of about 290 nm to 330 nm, and the effective dose is in the range of about 0.02 $J/cm^2$ to 1 $J/cm^2$. The effective dose can be greater than about two, three, five, or even ten minimal erythema doses (MED). The optical diagnostic signal can relate, or correspond, to diffuse reflectance or fluorescence, for example.

In another embodiment, the exposing step can include delivering a diagnostic dose of radiation from a source, wherein the diagnostic dose is sufficient to excite the fluorescence from the selected area, but is not an effective dose of phototherapeutic radiation, and wherein the delivering step includes delivering an effective phototherapeutic dose of radiation from the source by increasing fluence of the source.

The new method can further include detecting at least one additional optical diagnostic signal from the selected area; and determining from all of the signals whether the selected area is affected by the skin disorder. For example, at least two of the signals can relate to different physiological properties of the skin disorder. The method can further include constructing a digital map of areas of the patient's skin affected by the skin disorder by repeating the detecting and determining steps for additional selected areas; and delivering effective doses of phototherapeutic radiation, e.g., ultraviolet radiation, to at least one, some, or all of the affected areas indicated on the map.

In addition, the method can further include detecting an additional optical diagnostic signal from each of the areas indicated on the map to confirm that these areas are affected and designating the confirmed areas as treatment areas; and delivering an effective dose of phototherapeutic radiation to at least one of the treatment areas. For example, the constructing step can be completed before the delivering step.

In another aspect, the invention features a system for treating a proliferative skin disorder in a patient. The system includes an illumination source configured to irradiate the patient's skin; a detector configured to receive optical radiation emitted from selected areas of the patient's skin in response to the irradiation from the illumination source and to generate a signal relating to the radiation received from each of the selected areas (for example, the measured signal can include data relating to at least two different physiological features of the skin disorder); an analyzer connected to the detector, wherein the analyzer compares the signals from the selected areas to at least one threshold parameter and designates selected areas having measured signals above the threshold parameters as affected areas; and a source, e.g., a xenon chloride excimer laser, configured to deliver doses of therapeutic radiation designated by the analyzer.

In this system, the detector can measure diffuse reflectance and fluorescence and the analyzer can compare the signals relating to the diffuse reflectance and fluorescence to the at least one threshold parameter to designate the affected areas. In addition, the analyzer can normalize the measured signals when comparing them to the at least one threshold parameter.

Also, an automated positioning system can be connected to the analyzer and used to control the delivery of the doses from the source to the affected areas of skin designated by the analyzer. Alternatively, the analyzer can cause, e.g., directly cause, the therapeutic source to deliver the doses of therapeutic radiation to the affected areas of skin, e.g., through a manual instrument.

For example, the system can include a manual instrument connected to the therapeutic source and the detector such that the instrument delivers the optical radiation emitted from the selected areas of the patient's skin to the detector and delivers the doses of therapeutic radiation from the therapeutic source to the affected areas. In some embodiments, the manual instrument can be further connected to the illumination source to deliver illumination radiation to the patient's skin from the illumination source. The manual instrument can include one or more optical fibers through which the detector receives the optical radiation emitted from the selected areas of the patient's skin, and through which the therapeutic source delivers the doses of therapeutic radiation. The manual instrument can be in the shape of a pen or a comb. Also, the manual instrument can include a position sensor, which during operation sends a position signal to the analyzer to indicate a relative position of the instrument with respect to the patient. For example, the position sensor can be a tracking ball that rolls along the patient's skin as a doctor or technician positions the instrument.

A minimal erythema dose (MED) is defined as the lowest fluence eliciting an inflammatory response in normal skin. The MED varies from patient to patient and depends on natural skin color, as well as other factors, such as age and skin thickness. At 310 nm, the MED for Caucasians typically varies from about 0.05 to 0.30 $J/cm^2$, and the amount of energy required to provide one MED is higher in people having darker skin.

Measurement of diffuse reflectance is defined as measurement of a light component reflected from within the surface of a reflecting object. Multiple scattering within the object tends to depolarize the light component. To measure diffuse reflectance, one typically measures polarized light reflected from an object illuminated with orthogonally polarized light.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Embodiments of the invention include many advantages. For example, the methods and systems selectively deliver radiation to only those areas of skin affected by psoriasis, thereby reducing risks such as sunburn (acute risk) and skin cancer (chronic risk), which are inherent in present phototherapy methods. For example, scrotal cancer is about 200 times higher in patients subject to present phototherapy methods.

Furthermore, the methods and systems allow large doses of radiation to be delivered to the affected areas, which increases the effectiveness of the phototherapy. Furthermore, for these affected areas, skin cancer risk is reduced since only a few high-dose radiation treatments are used in place of many low-dose radiation treatments. Epidemiologic studies suggest that skin cancer risk is lower when a higher dose-per-treatment and lower cumulative dose is used.

Also, the methods and systems greatly reduce the number of treatments necessary to clear the psoriasis, from about 25 to about 5 to 10. The cost of psoriasis phototherapy is dominated by the number of treatments needed for clearing. As a result, in the United States, for example, the invention could save over one half of the annual phototherapy cost of about one billion dollars. The methods and systems also reduce the space and time required for each individual treatment, further reducing phototherapy costs. For example, since only affected areas are being treated, a doctor need not need be concerned about sunburning unaffected skin. Thus, before each treatment, the doctor need not determine the amount of radiation corresponding to one MED, as in traditional phototherapy.

Finally, the methods and systems automate the detailed and meticulous tasks of designating and selectively treating only those areas of skin affected by psoriasis or other disorders. The use of multiple diagnostics, which monitor different physiological features of skin, insures that areas of skin designated by all of the diagnostics are indeed affected, e.g., by psoriasis. The multiple diagnostics thereby prevent delivery of high-dose, and potentially harmful, radiation to unaffected areas of skin.

Other features and advantages of the invention will be apparent from the following detailed description, and from the claims.

DETAILED DESCRIPTION

Phototherapeutic Treatment

The invention features a method and device for delivering therapeutic ultraviolet (UV) radiation to plaques of psoriasis or other skin disorders, with little or no exposure to clinically normal skin. A collimated source of UV radiation scans, or is scanned, over a patient's body such that only plaques of psoriasis receive a therapeutic exposure dose of UV radiation.

Psoriasis responds best to UV radiation in a narrow wavelength region near 310 nm. At wavelengths longer than 310 nm, the effectiveness of radiation to treat psoriasis, i.e., the "action spectrum," is similar to the spectrum for delayed erythema (i.e., tanning). At wavelengths shorter than 300 nm, sunburn occurs much more quickly than clearing of psoriasis. See, for example, J. A. Parrish and K. F. Jaenicke in "Action spectrum for phototherapy of psoriasis" (*J. Invest. Dermatol.*, 76:336, 1981). High doses of UV radiation more effectively clears psoriasis. For example, exposing individual sites within plaques of psoriasis to a waveband near 310 nm clears the sites in an average of only 6 to 8 treatments at three minimal erythema doses (MED) per treatment, without any sunburn reactions in the plaque. Doses can be greater than about two MED, greater than about three MED, about ten MED, or greater than about ten MED. In particular, in some cases, psoriasis can be cleared in only one treatment with a dose of about sixteen MED. Even though doses at about eight to sixteen MED typically cause blisters or erosions of the skin, some patients do not mind such adverse effects given the rapid clearing of psoriasis at such doses. Nonetheless, to avoid such adverse effects, many patients should be treated at about two to five MED.

A suitable source for the collimated UV radiation is a xenon chloride (XeCl) excimer laser, which operates at about 308 nm. The skin is more sensitive to UV radiation at 308 nm than at 310 nm. At 308 nm, a therapeutic fluence ("dose") per treatment of about 1 to 10 MED is typically in the range of about 0.05–0.5 $J/cm^2$. These doses are much larger than those given in traditional phototherapy in which substantially all of a patient's skin is exposed to the radiation. The total laser energy involved in a treatment of a patient at these doses can be calculated as follows. An adult skin surface area is approximately 2 $m^2$ and a severe case of psoriasis affects about 50% of a patient's body. Therefore, the XeCl laser needs to deliver about 500–5000 J total energy. As a result, for a small XeCl laser running at 10 W average power (i.e., 10 J/s), the total treatment time (i.e., the time to cover the entire body) is about 50 to 500 seconds. The treatment times for larger XeCl lasers, e.g., operating at 100 W power, is less than about a minute.

An automated positioning system delivers the UV beam from the XeCl laser to the plaques of psoriasis on a patient's body. The positioning system operates in conjunction with one or more optical diagnostics, which determine the positions of the psoriasis plaques. In one embodiment, the positioning system and optical diagnostics operate together in "real time." That is, the optical diagnostics scan a selected area, and if the diagnostics determine that the selected area is affected with psoriasis, the positioning system delivers the radiation beam to the selected area immediately or shortly thereafter, e.g., before the optical diagnostic scans another selected area.

In another embodiment, an optical system first scans a substantial portion of an affected area or substantially all of the patient's body to construct a digital map of one or more optical diagnostic signals indicating affected and unaffected areas of skin. Thereafter, the positioning system delivers radiation to affected areas of skin according to the digital map. In this embodiment, a doctor can view and/or analyze the digital map before subjecting a patient to potentially harmful radiation. Based on the analysis, the doctor might modify parameters used to construct the map, and either repeat the diagnostic scans or reconstruct the digital map using the modified parameters and existing data from the diagnostic scans. Alternatively, the doctor might determine the parameters used in a real-time treatment based on the analysis. In a further embodiment, one or more diagnostics are used to generate the digital map and then the positioning system is directed to deliver radiation according to the map and one or more additional diagnostics, which are used in real time.

Since the positioning system delivers high doses of radiation in an automated manner, it is important that the optical diagnostics correctly determine the positions of the psoriasis plaques.

In other embodiments, a manual or hand-held device includes the optical diagnostics to automatically designate affected areas of skin and selectively treat only the affected areas of skin. In these embodiments, a surgeon rather than an automated positioning system scans the diagnostic and therapeutic radiation over the patient.

Optical Diagnostics

A number of diagnostics can be used to determine the positions of plaques caused by psoriasis or other proliferative skin disorders. Typically, a diagnostic is used to identify a physiological feature that distinguishes the plaques from unaffected skin. For example, psoriasis is an inflammatory disorder producing plaques that are "redder" than normal skin. The "redness" indicates increased blood content (erythema), which can be quantified using reflectance measurements.

In particular, erythema can be quantified by probing skin reflectance at or near the absorption bands of oxyhemoglobin ($HbO_2$) in the visible or near-infrared. To simplify analysis, "redness" can be measured as a ratio of diffuse reflectance from a selected area of skin for a pair of different wavelengths, i.e., a ratio of spectrally-resolved reflectance measurements. This ratiometric approach normalizes for spectrally-uniform differences in absolute reflectance from different areas of skin. A suitable pair of wavelengths includes a first wavelength at about 577 nm, where $HbO_2$ has a strong absorption band, and a second wavelength in the range of about 600 to 660 nm, where $HbO_2$ does not absorb strongly. Decreased reflectance of the 577 nm light relative to the redder 600 to 660 nm light indicates increased blood content. The ratio of reflectance measurements at these wavelengths is relatively independent of skin pigmentation.

Other pairs of wavelengths can also be used for spectrally-resolved reflectance measurements. For example, the oxygen saturation of hemoglobin in psoriasis plaques is significantly higher than that in unaffected areas of skin. Deoxyhemoglobin (Hb) absorbs more strongly than $HbO_2$ at about 815 nm, whereas $HbO_2$ absorbs more strongly at about 900 nm, so the ratio of reflectance at these wavelengths is also indicative of psoriasis.

In preferred embodiments, the reflectance measurements for psoriasis are made using a polarized light source. When the source irradiates a patient's skin, the reflected light has two components: a specular component or "glare" arising from the surface and a diffuse component backscattered from within skin tissue. The specular component remains substantially polarized, whereas the diffuse components becomes depolarized as a result of multiple scattering. Detecting reflected light that is polarized parallel to the polarized light source discriminates against the diffuse component, whereas detecting reflected light that is polarized orthogonal to the polarized light source discriminates against the specular component. The latter orientation is known as a measurement of "diffuse reflectance" and is preferred as a diagnostic of psoriasis since the diffuse component includes information about reflectance from within the skin tissue, e.g., from erythema. For more information about the examination of skin using polarized light, see: R.R. Anderson (*Arch. Dermatol.*, 127:1000–1005, 1991).

Another physiological feature of psoriasis is the proliferation of epidermal tissue. Tryptophan fluorescence increases, compared to normal skin, in plaques of psoriasis and other proliferative disorders including actinic keratosis and basal cell carcinomas (Kollias et al., U.S. Pat. No. 5,456,260). Tryptophan is the dominant aromatic amino acid fluorophore in skin. The tryptophan fluorescence is about three to ten times higher in plaques of psoriasis than in normal skin. Excitation of tryptophan fluorescence occurs in a broad band peaked near 290 nm and extending to approximately 320 nm and the fluorescence emission occurs in a broad band with a maximum near 355 nm. The cause of increased tryptophan fluorescence in psoriasis is unknown, but is likely to result from a combination of incomplete epidermal differentiation (expression of tryptophan-rich proteins near the skin surface) and increased epidermal thickness (greater optical pathlength in epidermis). These factors are not unique to psoriasis, but are always present in active plaques of psoriasis.

Since tryptophan fluorescence can be excited at a wavelength between 290 and 320 nm, a single (308 nm) XeCl excimer laser can provide low doses of radiation to excite tryptophan fluorescence and identify psoriasis plaques and provide high doses of radiation to treat the identified plaques. Light at 308 nm also excites dermal fluorophores such as collagen and elastin, whose fluorescent emissions can be used to normalize the tryptophan fluorescence. The fluorescent emission maxima for these dermal fluorophores occur near 370 nm (associated with both collagen and elastin), 390 nm (mostly associated with elastin), and 420 nm (mostly associated with collagen). Epidermal proliferation causes thickening of the epidermis, which partially blocks the excitation of these dermal fluorophores. Therefore, collagen and elastin emissions are lower in psoriasis than in normal skin. Accordingly, the ratio of tryptophan fluorescence, at for example 355 nm, and collagen or elastin fluorescence, at for example, 370 nm, 390 nm, or 420 nm, is a ratio that increases with epidermal proliferation and is indicative of psoriasis. Furthermore, the ratio is normalized to account for differences in absolute fluorescence.

Additional diagnostics can detect other physiological features of skin affected by psoriasis, such as increased blood flow, scaliness, decreased melanin pigmentation, and increased skin thickness. For example, doppler shifts in scattered laser light can indicate increased blood flow, increases in light scattering from the skin surface can indicate scaliness, spectrally-resolved reflectance can measure melanin pigmentation, and optical profilometry can measure skin thickness. In addition, dyes, topical treatments, or ingested compounds preferentially absorbed by either affected or unaffected areas of skin can be used to enhance optical determination of the positions of psoriasis plaques. For example, a topical treatment of dehydroxy acetone can give a patient a "fake" tan. As areas of skin affected with psoriasis shed, only unaffected areas of skin will remain tanned. The positions of the affected areas, which are not tanned, can be determined by reflectance measurements. In another example, tetracycline can be ingested by the patient. The tetracycline tends to bind to the epidermis and emits strong fluorescence. Since the epidermis is thicker in psoriasis plaques, the plaques will emit stronger fluorescence from tetracycline than areas unaffected with psoriasis.

The use of multiple diagnostics increases the certainty that the automated positioning system delivers radiation only to areas of the skin affected with psoriasis. For example, although increased erythema is a feature of psoriasis, it is also a feature of other red skin lesions such as hemangiomas, which are also known as "port wine stains." An automated system that delivers high doses of radiation based only on diffuse reflectance measurements that measure increased erythema would incorrectly diagnose the port wine stain as psoriasis and deliver potentially harmful radiation to the port wine stain. However, a port wine stain does not feature epidermal proliferation and a diagnostic measuring tryptophan fluorescence would correctly diagnose the port wine stain as unaffected by psoriasis. Conversely, a wart features epidermal proliferation but not increased erythema, and so independent diffuse reflectance and tryptophan fluorescence measurements would diagnose the wart as unaffected and affected, respectfully, by psoriasis. An automated system that delivers radiation only to areas in which both diffuse reflectance and tryptophan fluorescence diagnose psoriasis correctly distinguishes between a port wine stain, a wart, and actual psoriasis. Thus, an automated radiation system for psoriasis preferably includes two or more diagnostics that independently measure different physiological features of psoriasis.

An Automated Radiation System for Treatment of Psoriasis

Figure 1:
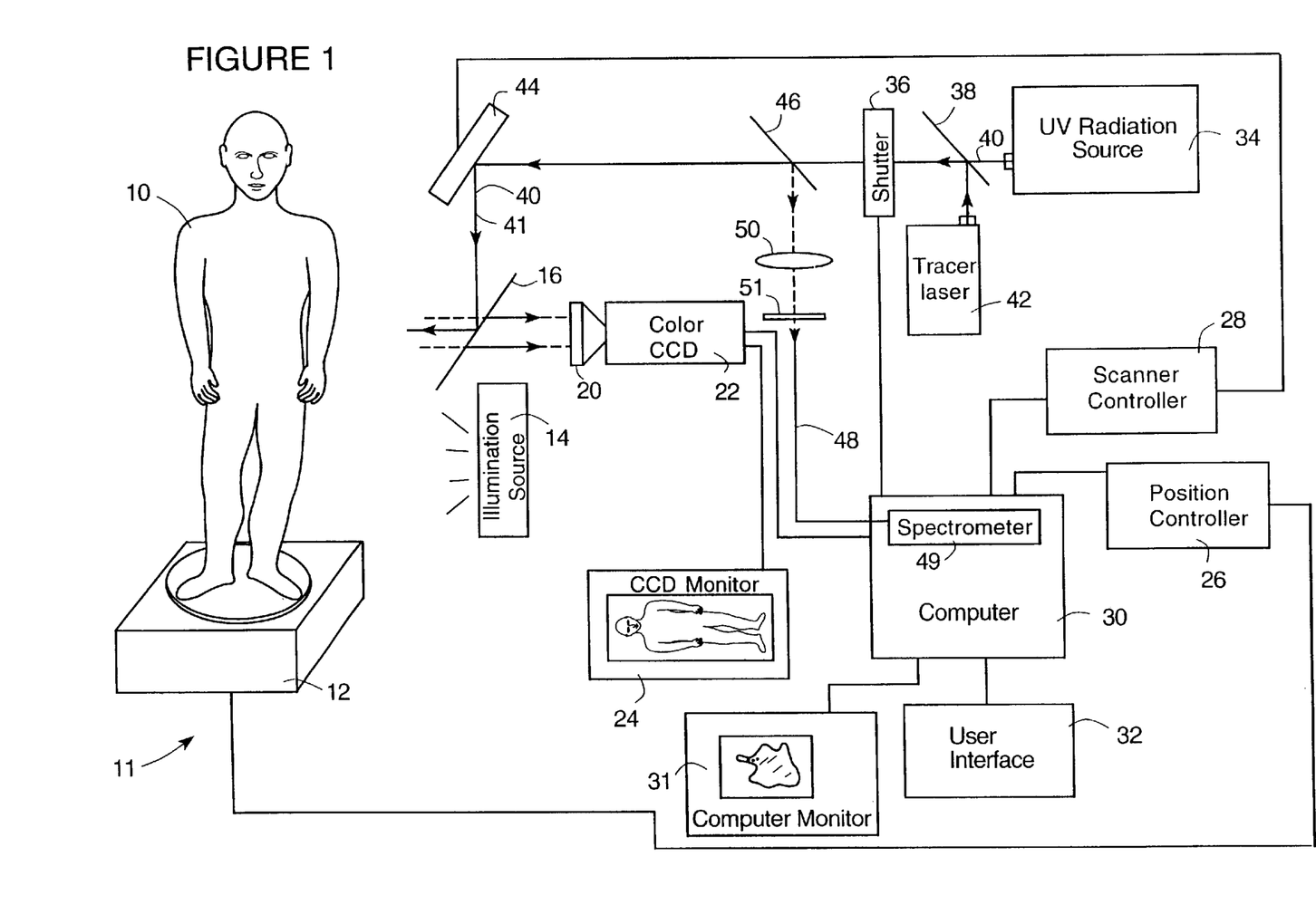
FIG. 1 is a schematic of an automated radiation system for treatment of inflammatory, proliferative skin disorders.

An automated system 11 for treating psoriasis using spectrally-resolved diffuse reflectance and tryptophan fluorescence diagnostics is shown in FIG. 1. Similar systems can be used to treat other inflammatory proliferative skin disorders. System 11 includes a position-controlled rotatable table 12 on which a patient 10 stands. The table can include handles (not shown) so that the patient can support him or herself and remain steady during the treatment. In other embodiments, the system can include a table on which a patients lies and which is ergonomically designed to increase patient comfort and reduce patient movement. An illumination source 14, which includes four 50 watt regulated tungsten-halogen lamps fitted with linear polarizers, illuminates the patient's skin with polarized light for viewing and reflectance measurements. A color charge-coupled device (color CCD) camera 22 captures light reflected from patient 10 and measures a real-time image of the patient's skin, which is displayed on a monitor 24. The light captured by CCD 22 is visible light (e.g., from about 450 nm to 700 nm) that passes through a dichroic mirror 16, which is substantially reflective in the UV and near UV (e.g., from about 290 nm to 440 nm) but only partially reflective in the visible. CCD 22 is fitted with a polarizer 20 oriented perpendicular to the polarization of the illuminating light so that CCD 22 measures diffuse reflectance from the patient's skin. In addition, a frame grabber stored in a computer 30 digitizes the image measured by CCD 22 and stores the image in computer 30 for subsequent processing.

A suitable color CCD 22 along with a standard frame grabber and accompanying image processing software is available from Pulnix (Sunnyvale, Calif.). Color CCD 22 includes three sets of detector arrays on the same silicon substrate. The detector arrays are covered with optical filters passing marginally-overlapping wavebands in the blue, green, and red parts of the visible spectrum, respectively. The frame grabber records data for each of the blue, green, and red arrays and stores the data in computer 30. CCD 22 provides real-time viewing of the patient's skin through monitor 24 and also records these images through its interface with computer 30. To diagnose areas of the patient's skin affected with psoriasis according to the "redness" of increased erythema, computer 30 divides the measured light intensity for each pixel in the red array by the measured light intensity for each corresponding pixel in the green array.

The size of the area of the patient's skin viewed by the CCD can be adjusted using various imaging optics (not shown) known in the art. In system 11, CCD 22 is positioned so that the image measured by CCD 22 spans the height of the position. To view and record diffuse reflectance images of different horizontal areas of the patient's skin (e.g., the patient's back versus the patient's stomach), position controller 26 rotates table 12. Position controller 26 connects to and is controlled by computer 30 using standard position controller software.

System 11 also includes a collimated ultraviolet radiation source 34, which provides therapeutic doses of ultraviolet radiation to affected areas of the patient's skin. Radiation source 34 is a nominally 10 W average power pulsed XeCl excimer laser operating at 100 to 1000 Hz providing a 308 nm treatment beam 40. One pulse from this XeCl laser, focused to a 3 mm spot size, corresponds approximately to about 1 MED. System 11 further includes a tracer laser 42, such as a small diode pumped Nd:YAG laser, which produces a low power, visible green (532 nm) tracer beam 41. A Dichroic mirror 38, which is transmissive for ultraviolet light (i.e., the 308 nm treatment beam) and reflective for visible light (e.g., the 532 nm tracer beam), combines tracer beam 41 with the treatment beam 40 making them exactly collinear with one another. Thereafter, a scanning mirror 44 and dichroic mirror 16 direct the treatment and tracer beams to the patient's skin. As described earlier, dichroic mirror 16 is substantially reflective in the UV and near UV and partially reflective in the visible. As a result, dichroic mirror 16 reflects substantially all of the treatment beam and a portion of the tracer beam toward the patient. The intensity of the portion of the tracer beam 41 reflected by mirror 16 is sufficient to produce a visible green spot on the patient. In most embodiments, the spot size of the tracer and treatment beams at the patient's skin is less than about 1 cm, and is typically about 1 to 4 mm. Focusing optics (not shown) can be used to produce desired beam spot sizes.

A scanner controller 28 adjusts the vertical angle of scanning mirror 44, thereby directing the treatment beam 40 (and collinear tracer beam 41) to different vertical positions of the patient's skin (after being reflected by dichroic mirror 16). Scanner controller 28 connects to and is controlled by computer 30 using standard scanner controller software. A suitable scanner system (scanning mirror(s), controller, and software) is available from General Scanning (Watertown, Mass.). Through its connections to scanner controller 28 and position controller 26, computer 30 can direct treatment beam 40 to substantially every area of a patient's skin.

Figure 2:
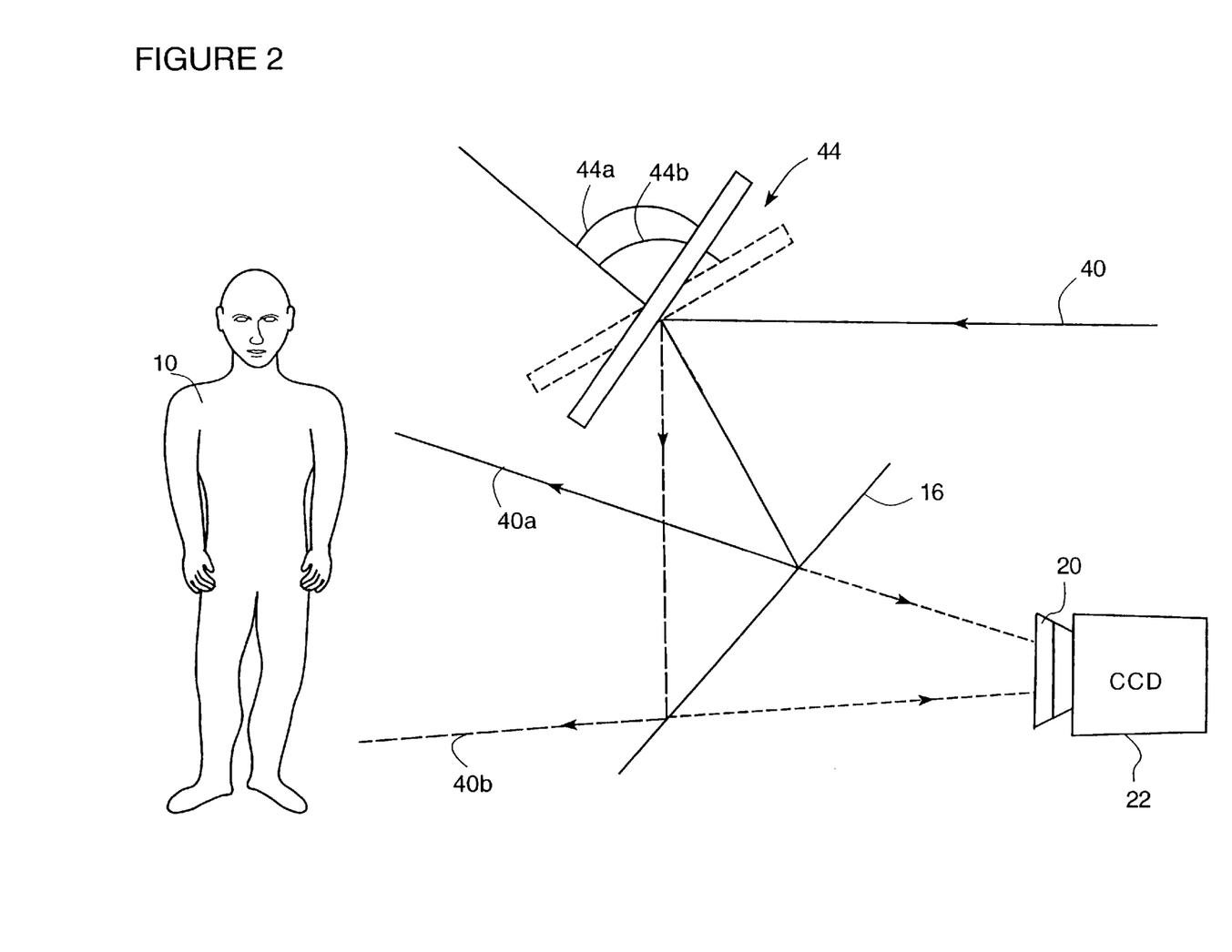
FIG. 2 is a schematic of a portion of the system in FIG. 1.

The distance between CCD 22 and dichroic mirror 16 should be exactly the same as the distance between scanning mirror 44 and dichroic mirror 16. As a result, CCD 22 receives light at the virtual plane of the scanning mirror 44. In this arrangement, the image measured by the CCD is measured as though the CCD was positioned in the path of the collinear treatment and tracer beams. Hence, there is no parallax between the CCD and the collinear treatment and tracer beams. In particular, each angle of the scanning mirror is in register with a pixel on the CCD, and this registration is independent of the patient's distance from the CCD and scanning mirror. This is illustrated in FIG. 2, which shows the treatment beam 40a and a virtual beam 43a detected by CCD 22, when scanning mirror 44 is at an angle 44a, and also shows the treatment beam 40b and a virtual beam 43b detected by CCD 22, when scanning mirror 44 is at an angle 44b.

Referring back to FIG. 1, CCD 22 detects the green tracer beam 41 when displaying images on monitor 24 and recording the images in computer 30. Since the green tracer beam is exactly collinear with the treatment beam, a doctor can observe the position of the treatment beam on the patient's skin using monitor 24. Furthermore, by recording the position of the tracer beam at multiple positions on the patient's skin, software in computer 30 can confirm the registration of the digital image recorded by the CCD 22 with the positioning of the treatment beam by scanner controller 28 via scanning mirror 44.

Shortly after being combined by dichroic mirror 38, treatment and tracer beams pass through a computer controlled shutter 36. Shutter 36 includes an adjustably-positioned screen having two apertures through which the beams can pass. Under control of computer 30, shutter positions the screen to block the beams, or pass the beams through one of the apertures. The first aperture completely transmits the beams. The second aperture is covered with a neutral (i.e., substantially spectrally uniform) optical density filter which partially transmits about one percent of the beams' energy. When the beams pass through the first aperture, shutter 36 transmits the full energy of the treatment and tracer beams, thereby delivering a therapeutic dose of UV radiation from source 34 to the patient's skin. When the beams pass through the second aperture, shutter 36 delivers a dose of UV radiation to the patient's skin that is sufficient to excite tryptophan fluorescence, but not sufficient to damage or harm the patient's skin (i.e., a diagnostic dose). During operation, scanning mirror 44 and controller 28 raster treatment beam 40 and tracer beam 41 along the patient's body at a fast rate (e.g., about 4 to 40 mm/ms). The appearance of the tracer beam on monitor 24 will toggle between bright and dim, depending on whether treatment beam is delivering a therapeutic (and potentially harmful) dose of UV radiation or a diagnostic (and safe) dose of UV radiation.

A partially reflecting dichroic mirror 46 directs fluorescence and diffuse reflectance (of light from the illumination source 14) from the area of skin excited by the treatment beam to an optical fiber 48, which is coupled to a spectrometer board 49 (Ocean Optics, Fla.) in computer 30. The light reaching fiber 48 is directed toward dichroic mirror 46 by dichroic mirror 16 and scanning mirror 44. Mirror 46 is transmissive at 308 nm, the wavelength of UV source 34, but partially reflective for longer wavelengths in the near UV and visible (i.e., longer than about 330 nm). A lens 50 is positioned to couple only fluorescence and reflectance from the area of skin coincident with treatment beam 40 into fiber 48. A polarizer 51 oriented perpendicular to the polarization of the light from illumination source 14 is positioned immediately before fiber 48 so that spectrometer board 49 measures only diffuse reflectance.

To monitor epidermal proliferation, the spectrometer records tryptophan fluorescence at 355 nm relative to collagen fluorescence at 420 nm and stores the data in computer 30 for subsequent processing. To monitor increased erythema, the spectrometer records diffuse reflectance at about 577 nm (a strong absorption band of $HbO_2$) relative to about 640 nm (only weak absorption by $HbO_2$) and stores the data in computer 30 for subsequent processing. This second set of data can be used together with or instead of the red and green array images recorded by CCD 22. Standard software (also available from Ocean Optics) stored in computer 30 can process the spectroscopic data from spectrometer board 49.

System 11 also includes a user interface 32, which is connected to computer 30. User interface 32 allows input of user-specified threshold parameters, specifications for display of recorded images and data, parameters for the shutter, treatment beam, spectrometer board, and scanning and position controllers. User interface 32 also includes a "kill-switch" that immediately closes shutter 36 and terminates delivery of therapeutic doses of radiation to the patient.

System 11 can be modified in many ways. For example, different collimated UV sources (e.g., collimated beams from an arc lamp such as xenon, mercury, and xenon-mercury, and excimer lasers such as HeCd, frequency-tripled Nd:YAG or Ti:Sapphire, and nitrogen lasers), different illumination sources (e.g., fluorescent lamps, incandescent lamps, and visible lasers), and different tracer lasers (e.g., low-power HeNe, diode, and dye lasers) can be used. Also, rather than a color CCD camera, other digitizing cameras (e.g., array detectors and charge injection device (CID) detector) can be used. The shutter can be a mechanical, electro-optic, acousto-optic, or liquid-crystal shutter. Alternatively, rather than using a shutter, the computer can modulate the output of the UV radiation source and tracer laser directly, e.g., by current or voltage regulation. Different types of imaging, scanning, and positioning systems can also be used. For example, rather than scanning mirrors, beam delivery and fluorescence and reflectance capture can be accomplished by fiber bundles mounted on x-y, or even x-y-z, computer-controlled translation stages. The CCD camera could also be mounted on these stages. Also, different types of spectrometers can be used, such as a large scale monochrometer fitted with an array detector. In any of the optical measurements, sensitivity and dynamic range can be increased using lock-in detection and photon counting techniques, as well as other techniques known in the art.

Operating the Automated Treatment System

About a day before treatment, a patient applies a alpha-hydroxy acid, such as salicylic or lactic acid, to affected areas of skin to descale the psoriasis plaques. After showering the following day and before treatment, the patient then applies an index-matching lubricant, such as mineral oil, to enhance the optical diagnostics. Thereafter, once the patient is positioned on table 12 and illumination source 14 illuminates the patient, treatment can begin.

Computer 30 stores a computer readable program (i.e., software) that executes on a processor in the computer to operate system 11. The program works together with commercially available software stored in the computer for operating spectrometer board 49, scanner controller 28, position controller 26, shutter 36, and CCD 22. According to the program, system 11 can operate in a number of modes. In a first mode, the system performs the steps shown in FIG. 3 and described below.

Figure 3:
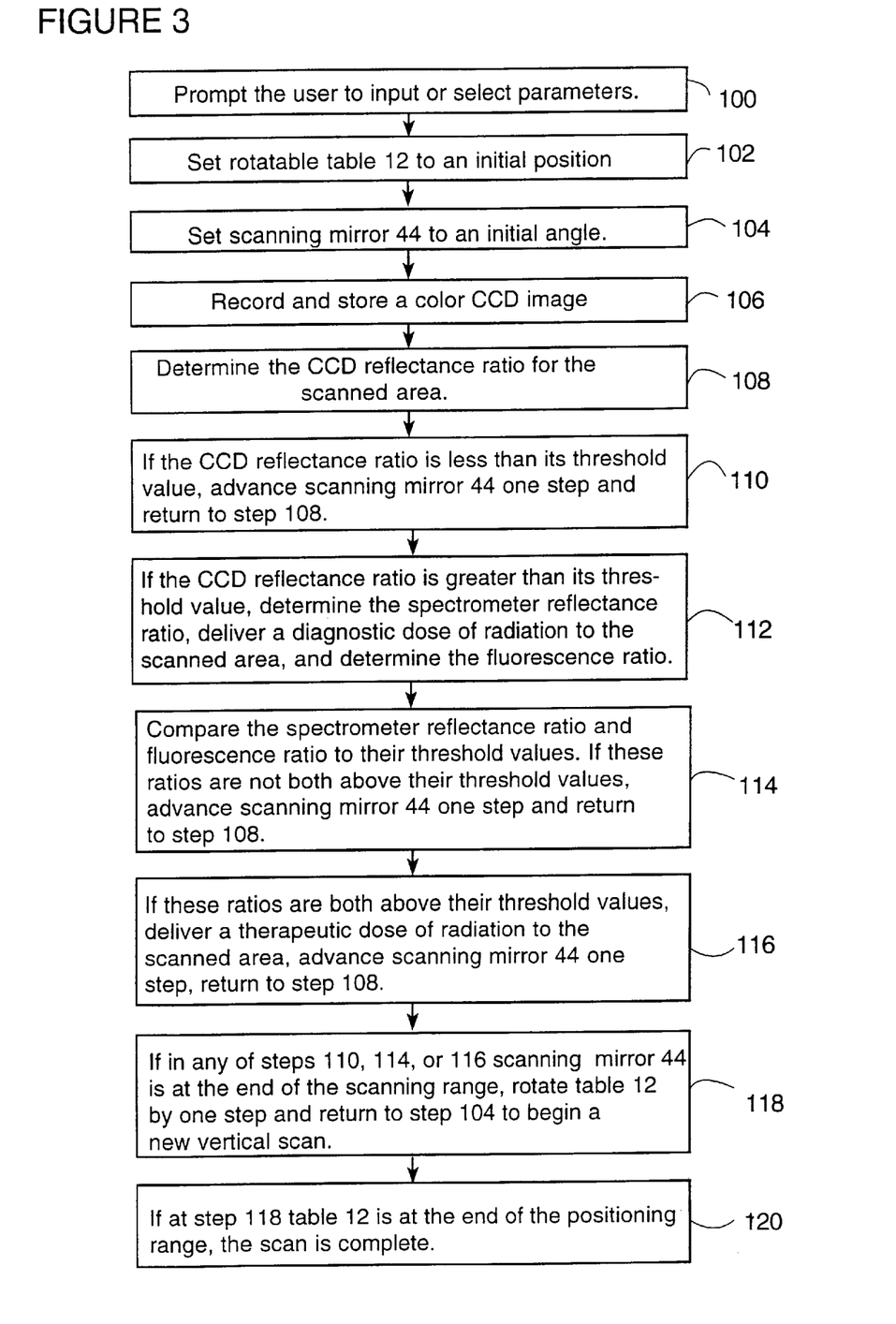
FIG. 3 is a flow diagram of the steps performed by a computer executing software for operating the system shown in FIG. 1 when in a treatment mode.

First, computer 30 prompts the user to input or select parameters for the treatment fluence for the UV source, scanning and positioning ranges for scanner controller 28 and position controller 26, and thresholds for the optical diagnostics (step 100). For system 11, there are three diagnostics. The first diagnostic provides the ratio (CCD reflectance ratio) of the diffuse reflectance measured by a pixel on the red array of CCD 22 divided by the diffuse reflectance measured by the corresponding pixel on the green array of CCD 22. The second diagnostic provides the ratio (spectrometer reflectance ratio) of the 640 nm to 577 nm diffuse reflectance measured by the fiber spectrometer 49. Both CCD and spectrometer reflectance ratios are measurements of increased erythema, i.e., "redness." The third diagnostic provides the ratio (fluorescence ratio) of the 355 nm to 420 nm fluorescence measured by spectrometer board 49. The fluorescence ratio is a measurement of epidermal proliferation as indicated by increased tryptophan fluorescence. These ratios are examples of optical diagnostic signals that relate to physiological features of psoriasis. For each of these ratios, the program prompts the user to input into the computer a threshold value, or select from a number of preprogrammed threshold values, for which a measured ratio greater than the threshold ratio indicates a physiological feature of psoriasis.

In the next step, computer 30 sends a signal to position controller 26 to set rotatable table 12 to the initial "x" (horizontal) position specified by the positioning range (step 102), and then sends a signal to scanner controller 28 to set scanning mirror 44 to an initial "y" (vertical) position specified by the scanning range (step 104). Thereafter, computer 30 records and stores a color digital image of the patient's skin measured by CCD 22 (step 106). Then, computer 30 determines the CCD reflectance ratio for the pixel corresponding to the area of skin pointed to by scanning mirror 44, i.e., the scanned area (step 108). If that ratio is less than the corresponding user-defined threshold value, computer 30 instructs scanning controller 28 to advance scanning mirror 44 one vertical step (i.e., by adjusting the angle of the scanning mirror) and returns the program to step 108 (step 110). If that ratio is greater than the corresponding user-defined threshold value, computer 30 determines the spectrometer reflectance ratio, then opens shutter 36 to deliver a diagnostic dose of radiation to the scanned area, and thereafter determines the fluorescence ratio (step 112).

In the next step, computer 30 compares the spectrometer reflectance ratio and fluorescence ratio to their corresponding threshold values. If these ratios are not both above their respective threshold values, computer 30 instructs scanning controller 28 to advance scanning mirror 44 one vertical step and returns the program to step 108 (step 114). If these ratios are both above their respective threshold values, computer 30 opens shutter 36 to deliver a therapeutic dose of radiation to the scanned area and then instructs scanning controller 28 to advance scanning mirror 44 one vertical step and returns the program to step 108 (step 116).

If in any of steps 110, 114, or 116, scanning controller 28 determines that scanning mirror 44 is at the end of the scanning range, it sends a "scanning end of range" signal to computer 30, which then instructs position control 26 to advance (e.g., rotate or step) table 12 by one horizontal step and returns the program to step 104 to begin a new vertical scan (step 118). If at step 118, position controller 26 determines that rotatable table 12 is at the end of the positioning range, it sends a "positioning end of range" signal to computer 30 indicating that the scan is complete and computer 30 ends the treatment (step 120).

Throughout the scan, the user (i.e., the doctor or technician) can observe the patient's skin and tracer beam on the real-time image displayed on monitor 24. The green tracer beam is visible only after the CCD reflectance ratio indicates the scanned area has increased erythema or redness, since it is only then that shutter 36 is opened to deliver a diagnostic dose of radiation. If the user observes on monitor 24 that the tracer beam is not on a "red" plaque, it indicates that the threshold value for the CCD reflectance ratio is too low or that the tracer and treatment beams are not in register with the CCD image. In either case, the user can terminate the treatment using the "kill-switch."

The tracer beam goes from dim to bright once a therapeutic dose of radiation is delivered to the scanned area. If the user, based on the real-time image on monitor 24, determines that a therapeutic dose should not be delivered to the area highlighted by the bright green tracer beam, the user immediately terminates treatment using the "kill-switch." The scenario may occur if the threshold values for the diagnostic ratios are too low or if the diagnostics identify areas of skin that have both "redness" and epidermal proliferation but are still not affected by psoriasis epidermis. Conversely, the user may determine that areas of skin that appear to be affected by psoriasis are not being treated. In this case, one or more of the threshold values may be too high.

In some cases, the user will set the threshold values for the CCD reflectance ratio relatively lower than the spectrometer reflectance ratio. As a result, the CCD reflectance ratio provides a crude sensitivity to "red" areas and guides the scanner to these areas, as indicated by the dim tracer beam. Once in these areas, the spectrometer reflectance ratio and fluorescence ratio provide more sensitive diagnostics of physiological features indicative of psoriasis.

To properly determine the threshold values, which may vary from patient to patient or with the severity of the psoriasis, the program can operate in a second (diagnostic) mode. In the second mode, no treatment is delivered to the patient and the system performs the steps shown in FIG. 4 and described below.

Figure 4:
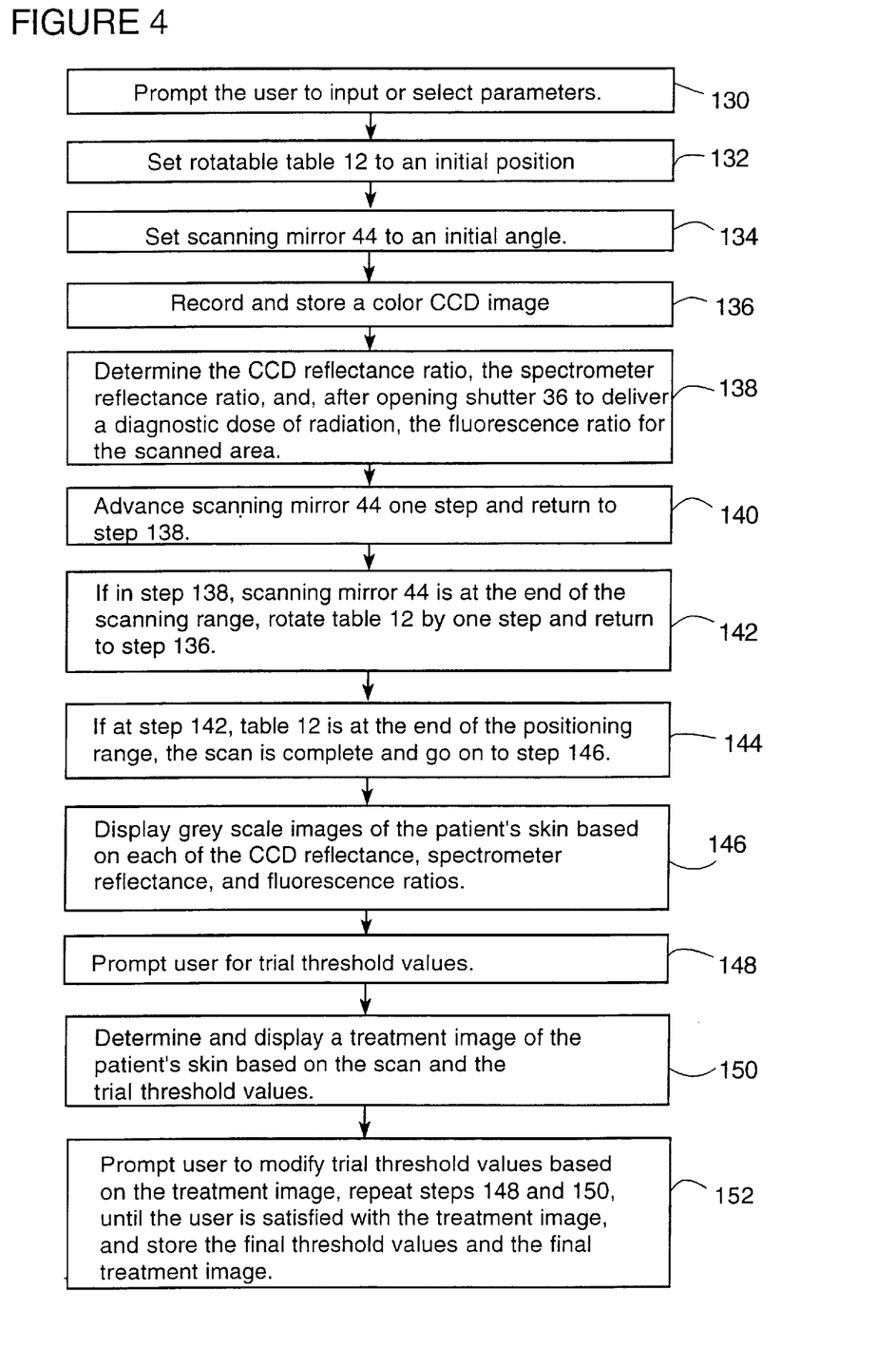
FIG. 4 is flow diagram of the steps performed by a computer executing software for operating the system shown in FIG. 1 when in a diagnostic mode.

After a patient is positioned on table 12 and illumination source 14 irradiates the patient, computer 30 prompts the user to input scanning and positioning ranges for scanner controller 28 and position controller 26 (step 130). In the next step, computer 30 sends a signal to position controller 26 to set rotatable table 12 to the initial "x" (horizontal) position specified by the positioning range (step 132), and then sends a signal to scanner controller 28 to set scanning mirror 44 to an initial "y" (vertical) position specified by the scanning range (step 134). Thereafter, computer 30 records and stores a color digital image of the patient's skin measured by CCD 22 (step 136). In the next step, for the scanned area, computer 30 determines and records the CCD reflectance ratio from the recorded image, the spectrometer reflectance ratio from measurements by spectrometer board 49, and, after opening shutter 36 to deliver a diagnostic dose of radiation, the fluorescence ratio from measurements by spectrometer board 49 (step 138). Computer 30 then instructs scanning controller 28 to advance scanning mirror 44 one vertical step and returns the program to step 138 (step 140).

If in step 138, scanning controller 28 determines that scanning mirror 44 is at the end of the scanning range, it sends a "scanning end of range" signal to computer 30, which then instructs position control 26 to advance (e.g., rotate or step) table 12 by one horizontal step and returns the program to step 136 to begin a new vertical scan (step 142). If at step 142, position controller 26 determines that rotatable table 12 is at the end of the positioning range, it sends a "positioning end of range" signal to computer 30 indicating that the scan is complete (step 144).

Once the scan is complete, computer 30 displays on a computer monitor 31 grey scale images of the patient's skin based on each of the CCD reflectance, spectrometer reflectance, and fluorescence ratios (step 146). Computer 30 then prompts the user for trial threshold values (step 148). Thereafter, computer 30 determines and displays a "treatment" image of the patient's skin that highlights areas of skin that would be treated based on the trial threshold values and the diagnostic ratios from the scan (step 150). Based on the grey scale images and the treatment image, the user modifies the trial threshold values. The program then repeats steps 148 and 150, until the user is satisfied with the treatment image, at which point computer 30 stores the final threshold values and the final treatment image (step 152). These threshold values can be used in a subsequent treatment scan for the same patient in which the program operates in the first mode, as shown in FIG. 3.

Alternatively, the program can operate in a third mode in which the final treatment image is used as a "treatment map" in a subsequent treatment scan. In the third mode, the program performs the steps shown in FIG. 5 and described below.

Figure 5:
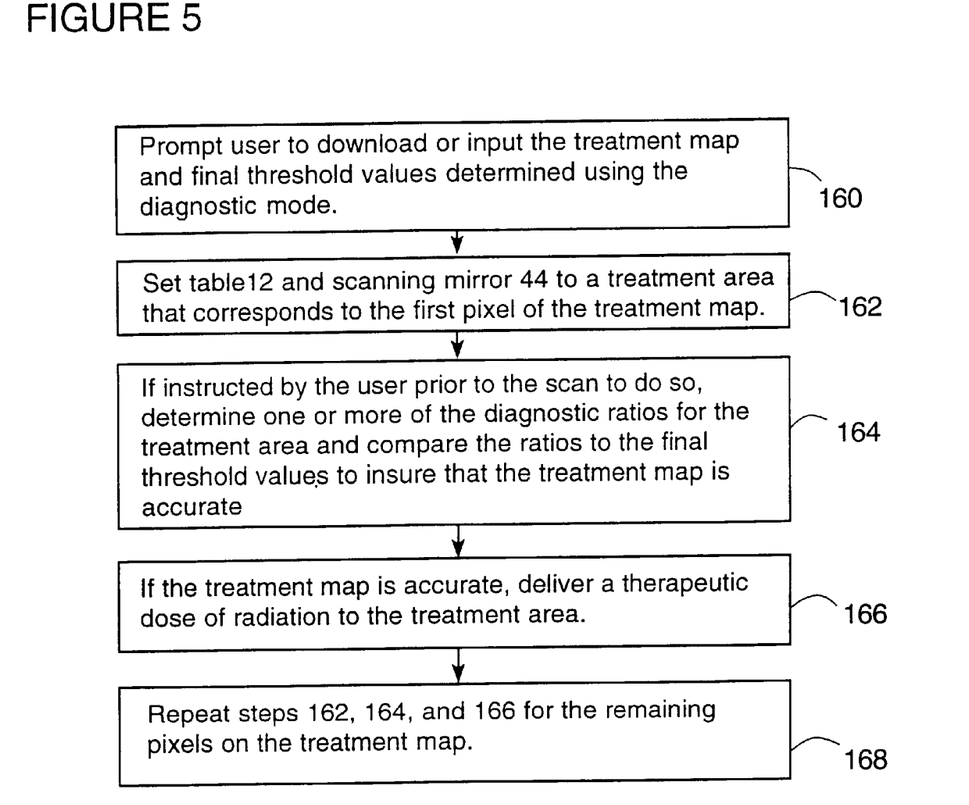
FIG. 5 is a flow diagram of the steps performed by a computer executing software for operating the system shown in FIG. 1 when in a map-guided treatment mode.

First, computer 30 recalls or prompts the user to download or input the treatment map and final threshold values determined for the patient using the diagnostic mode of the program described above with respect to FIG. 4 (step 160). Computer 30 then sends a signal to the position controller 26 and scanner controller 28 to set table 12 and scanning mirror 44 to a treatment area that corresponds to the first pixel of the treatment map (step 162). Then, if prompted by the user prior to the scan, computer 30 determines one or more of the diagnostic ratios for the treatment area and compares these ratios to the final threshold values to insure that the treatment map is accurate for the current scan (step 164). If the treatment map is accurate, computer 30 opens shutter 36 and UV source 34 delivers a therapeutic dose of radiation to the treatment area (step 166). Then, the computer repeats steps 162, 164, and 166 for the remaining pixels on the treatment map (step 168).

In other embodiments, the program can be modified in various ways. For example, after recording the CCD image, computer 30 can determine a CCD reflectance ratio for every pixel corresponding to the areas of skin within the scanning range for the current position of rotatable table 12, i.e., all the pixels in a vertical line scan. Thereafter, computer 30 instructs scanner controller 28 to step-wise scan only those areas of the line scan designated as affected areas by the CCD reflectance ratios.

In another example, once a phototherapeutic dose of radiation is delivered to an affected area, computer 30 instructs shutter 36 to remain completely open and deliver phototherapeutic doses to subsequent areas until the diagnostic ratios indicate that the scanned area is not an affected area. In these cases, computer 30 uses the fluorescence produced by the phototherapeutic dose of radiation to determine the fluorescence ratio. With this modification, the computer more rapidly treats affected areas within psoriasis plaques since shutter 36 does not mechanically adjust the screen to deliver a diagnostic and therapeutic dose of radiation for each affected area.

In further examples, the computer can vary the fluence of the therapeutic dose for each treatment area (by controlling the shutter) according to the differences of the diagnostic ratios from the threshold values. Alternatively, or in addition, the computer can deliver a therapeutic dose only when one or more of the diagnostic ratios are within user-specified threshold ranges, i.e., ranges having upper and lower limits. Also, to simplify the procedure, the computer need evaluate only a single diagnostic for diffuse reflectance, i.e., the CCD reflectance ratio or the spectrometer reflectance ratio.

The optical diagnostic signals can also be different than the empirically-normalized ratios described above. For example, absolute values can be used, or absolute values that are theoretically normalized (e.g., by theoretically compensating for the fluorescence dependence on the incident angle of the treatment beam). Also, the diagnostic signals can be ratios that include background corrections, e.g., they can be determined from three spectral signals according to the form (A-B)/C, where "B" subtracts the background from the spectral signal of interest "A," and "C" normalizes the background-free signal. In general, complex control routines can be implemented based on the feedback from the diagnostic measurements.

Furthermore, analysis of the CCD images can be enhanced by using a number of techniques known in the art. For example, "edge enhancement" of lesions can be implemented by analysis of the derivative of a given diagnostic between adjacent pixels or groups of pixels. The ranges of values for each pixel can be adjusted to optimize the dynamic range of a given diagnostic. "Bad" pixels due to CCD defects and/or noise can be recognized using global or local statistical methods, and eliminated or assigned local average values. "Smoothing" algorithms can also be used to reduce high spatial frequency variations.

Manual Systems

Manual devices can also be used to impart the automated treatment described above. As in the systems described above, the manual device includes one or more optical diagnostics to designate affected areas of skin and guide treatment of the affected areas. During operation, an operator manually scans the device over regions of proliferative skin disease and the optical diagnostics determine which regions should be treated with therapeutic radiation. In this way, the manual systems are identical to the systems described previously, except that the operator and not an automatic positioning system scans the diagnostic and therapeutic radiation over the patient. In a different embodiment of the manual device, an operator manually positions the device between regions containing skin disease and the device itself scans the diagnostic and therapeutic radiation within each region.

Figure 6A:
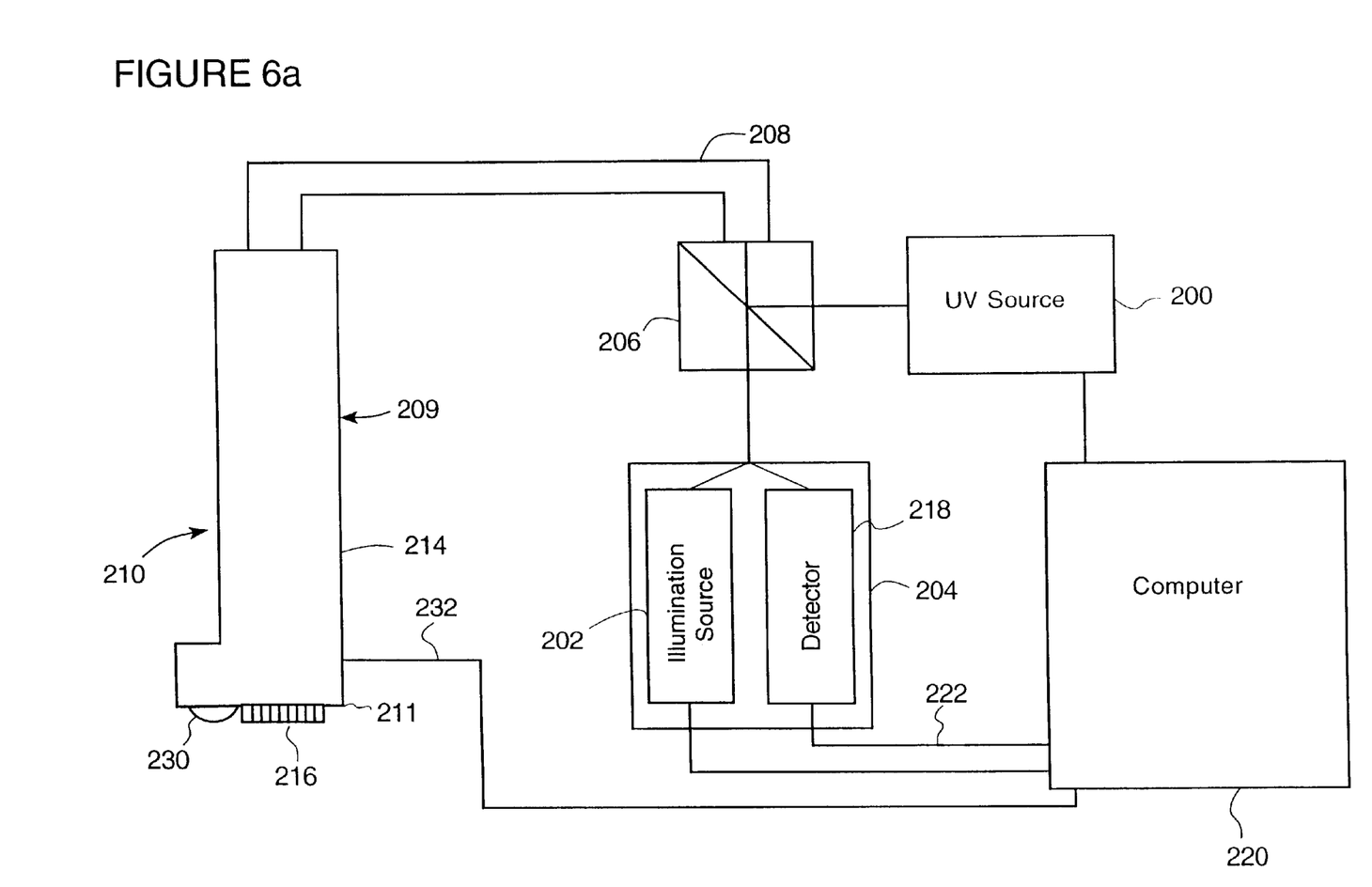
FIGS. 6a and 6b are schematic diagrams of a fiber optic pen system for the automated designation and treatment of a proliferative skin disease.

One example of a manual device providing the automated treatment is the fiber optic pen system shown in FIG. 6A. A UV radiation source 200 provides therapeutic radiation, and an illumination source 202 in a diagnostic system 204 provides diagnostic radiation, to a dichroic beamsplitter 206, which combines the diagnostic and therapeutic radiation and couples it into a fiber optic bundle 208. The fiber optic bundle is attached to a pen-shaped support 209 to form a fiber optic pen 210. The distal end 211 of pen 210 exposes the multiple fibers of fiber optic bundle 208.

Figure 6B:
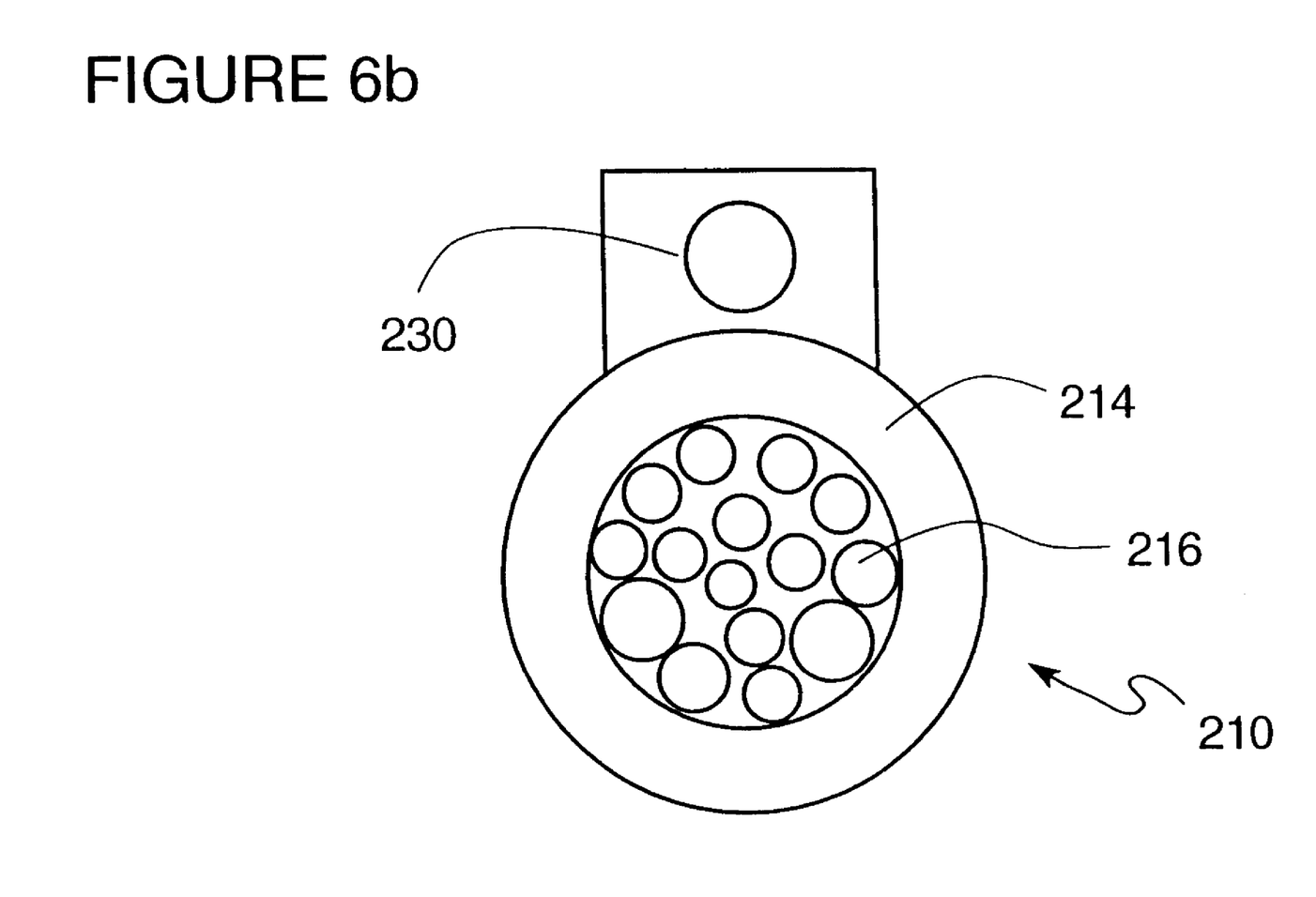

As shown in FIG. 6B, which is a cross-sectional diagram of the distal end of fiber optic pen 210, support 209 includes an outer cylindrical shell 214 surrounding and enclosing the multiple optical fibers 216, but leaving the ends of the fibers exposed at distal end 211 of pen 210.

During use, pen 210 is passed over a patient's skin and exposed optical fibers 216 deliver therapeutic and diagnostic radiation to, and receive diagnostic signal radiation, e.g., fluorescence or diffuse reflectance, from, regions of the skin. The optical fibers 216 deliver the diagnostic signal radiation to a detector 218 in diagnostic system 204 via fiber optical bundle 208 and dichroic beamsplitter 206. A computer 220 controls both UV radiation source 200 and diagnostic system 204 and receives a diagnostic signal 222 from detector 218 indicative of the diagnostic signal radiation. Based on signal 222, computer 220 determines whether to cause UV radiation source 200 to deliver a dose of therapeutic radiation to the region of skin probed by the diagnostic radiation for automated, real time operation. Alternatively, as in the system of FIG. 1, computer 220 can produce a treatment map of affected regions of skin based on signal 222 for subsequent use in delivering therapeutic doses of UV radiation to the affected regions ("treatment map" operation).

The basis for diagnosing regions of skin affected with skin disease and suitable sources for the therapeutic and diagnostic radiation are the same as those described previously for the system of FIG. 1. For example, UV source 200 can be an XeCl excimer laser operating at 308 nm and illumination source 202 can be a tungsten-halogen lamp equipped with linear polarizers to provide polarized white light. Computer 220 can operate UV source 200 in a low power diagnosis mode, which provides diagnostic radiation that can excite tryptophan fluorescence at, e.g., 355 nm, and collagen or elastin fluorescence at, e.g., 370 nm, 390 nm, or 420 nm. As described previously, a change in tryptophan fluorescence relative to collagen or elastin fluorescence indicates an increase in epidermal proliferation, which is a symptom of psoriasis. In addition, as also described previously, the polarized white light from illumination source 202 can be diffusely reflected from the patient's skin to provide a diagnostic of the characteristic "redness" of psoriasis by comparing the ratio of diffuse reflectance at, e.g., 576 nm and 610 nm. The diagnostic signal radiation delivered to detector 218 via the fibers includes diagnostic signal radiation caused by both fluorescence and diffuse reflectance. Detector 218 includes a spectrometer that measures the intensities of the fluorescence and diffuse reflectance at the appropriate wavelengths. Detector 218 sends these intensities to computer 220 for analysis.

Using the fluorescence and diffuse reflectance data from detector 218, computer 220 determines whether the region of skin scanned by the pen is affected with a skin disease such as psoriasis. If so, and if the fiber optic pen system is operating in a real-time mode, computer 220 causes UV source 200 to deliver a therapeutic dose of UV radiation to the patient's skin via fiber optic pen 210.

To insure that the proper amount of therapeutic radiation is delivered to affected areas of skin as the pen is scanned over the patient, fiber optic pen 210 includes a position sensor 230 at its distal end 211 to monitor the scanning speed. For example, the position sensor can be a tracking ball that rolls as the pen 210 is scanned over a patient's skin. The position sensor 230 sends a position signal 232 to computer 220 indicative of the scanning speed. Based on the scanning speed, computer 220 causes UV source 200 to vary the intensity of the therapeutic radiation so that the total exposure administered to a particular region of affected skin provides a therapeutic dose. For example, if an operator scans a patient more slowly with pen 210, computer 220 causes UV source 200 to reduce the power of the therapeutic radiation so that the total exposure per unit area remains constant.

Position sensor 230 also permits pen 210 to operate in a "treatment map" operation in which computer 220 compares position signal 232 and diagnostic signal 222 to construct a treatment map of the affected areas of skin. The treatment map can be used in subsequent treatment of the affected areas by directing the operator as to where to scan the pen over the patient when in a mode of operation in which the pen delivers therapeutic doses of radiation to the patient.

In the presently described embodiment, each fiber 216 in fiber optic bundle 208 carries therapeutic and diagnostic radiation to the skin and receives diagnostic signal radiation from the skin. In alternative embodiments, individual fibers within the fiber optic bundle may deliver only diagnostic radiation, deliver only therapeutic radiation, receive only diagnostic signal radiation, or some combination thereof. Also, rather than using a plurality of fibers in a fiber optic bundle, other embodiments of the fiber optic pen can include only a single fiber for delivering and receiving radiation, or alternatively, a single fiber for each of delivering diagnostic radiation, delivering therapeutic radiation, and receiving diagnostic signal radiation, or some combination thereof.

One application for which a manual or handheld device is particularly suitable is for the treatment of proliferative skin diseases, e.g., psoriasis of the scalp. Hair on the scalp complicates treatment of the skin disease, often requiring removal of the hair or more time-consuming treatments in which the hair is manipulated to expose each treatment area. To avoid such complications, the fiber optic pen described above can be used. Alternatively, a fiber optic comb such as the one described in U.S. Pat. No. 5,300,097 can be modified to perform the new optical diagnostic methods described herein and to provide selective delivery of therapeutic radiation by the comb.

Figure 7:
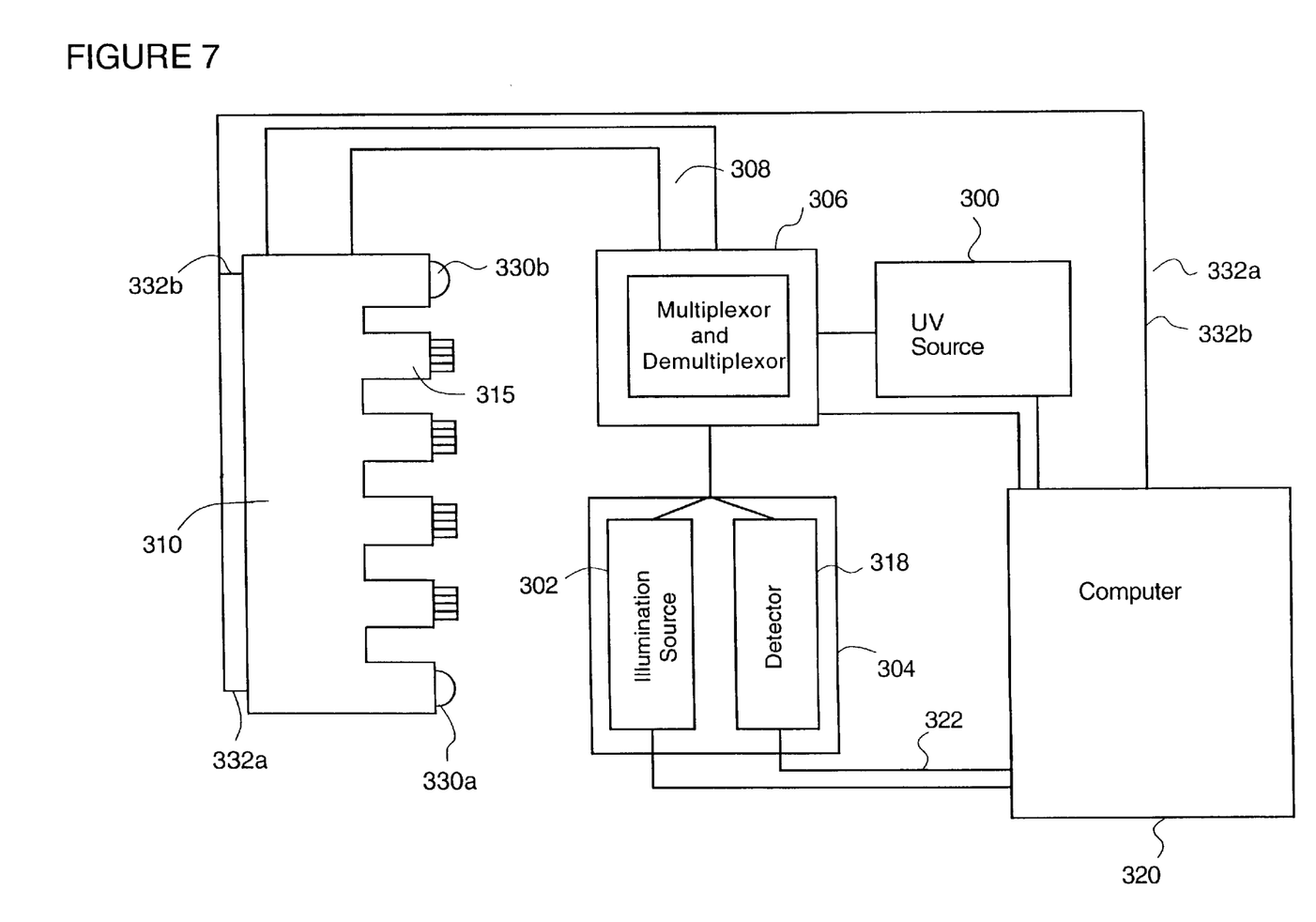
FIG. 7 is a schematic diagram of a fiber optic comb system for the automated designation and treatment of a proliferative skin disease.

A schematic diagram of such a fiber optic comb 310 is shown in FIG. 7. Comb 310 can operate in a manner similarly to that of pen 210. A UV radiation source 300 and an illumination source 302 in a diagnostic system 304 provide therapeutic and diagnostic radiation to a optical multiplexor and demultiplexor 306. The optical multiplexor and demultiplexor directs the radiation to a fiber optic bundle 308, which extends into comb 310. In comb 310, the fibers in bundle 308 are split into portions that each extend to a corresponding prong or tooth 315 of comb 310. Each prong 315 is equivalent to the fiber optic pen 210 described above, delivering diagnostic and therapeutic radiation and receiving diagnostic signal radiation from the skin, e.g., fluorescence or diffuse reflectance. Diagnostic signal radiation received by each prong 315 is delivered to a detector 318 in diagnostic system 304 via fiber optic bundle 308 and optical multiplexor and demultiplexor 306.

As in the fiber optic pen system described above, a computer 320 controls both UV radiation source 300 and diagnostic system 304 and receives a diagnostic signal 322 from detector 318 indicative of the diagnostic signal radiation received from the skin by each prong. Based on signal 322, computer 320 determines whether to cause UV radiation source 300 to deliver a dose of therapeutic radiation to the region of skin probed by the diagnostic radiation (real-time operation). Alternatively, as in the system of FIG. 1, computer 320 can produce a treatment map of affected regions of skin based on signal 322 for subsequent use in delivering therapeutic doses of UV radiation to the affected regions ("treatment map" operation).

Computer 320 also controls optical multiplexor and demultiplexor 306, which insures that radiation being sent to comb 310 is delivered to the correct prong and informs computer 320 which prong sent which particular diagnostic signal. To do this, optical multiplexor and demultiplexor 306 can use electro-optic scanning and optical switching techniques known in the art, e.g., through piezo-electrical, electro-optical, acousto-optical, or electro-mechanical manipulation of optics guiding the radiation.

For example, to direct a single optical input signal into one of a number of optical output channels (e.g., an array of fibers), the optical multiplexor and demultiplexor can include a shutter, a timing circuit, and a galvanometric mirror. The input signal passes through the shutter and then onto the galvanometric mirror, which continuously scans the input signal across the output channels. To direct the input signal into a selected output channel, the timing circuit only opens the shutter when the galvanometric mirror directs the input signal into the selected output channel. Such a system can also be used in the opposite direction to select an optical signal from one of many input channels. Suitable galvanometric scanning systems are available from General Scanning, Inc. (Watertown, Mass.).

Comb 310 also includes one or more position sensors to track its position and speed as it is being scanned over a position. For example, comb 310 can include position sensors 330a and 330b, e.g., tracking balls, at opposite ends of comb 310. The position sensors specify changes in the position and orientation of comb 310, thereby specifying the position of each prong 315. Position sensors send signals via conduits 332a and 332b to computer 320, which monitors the position of each prong. As described with regard to pen 210, in "real time" operation, computer 320 controls the power of the therapeutic radiation delivered by UV source 300 to compensate for changes in scanning speed. Similarly, in "treatment map" operation, computer 320 compares the diagnostic signals 322 and position signals 332a and 332b to generate a treatment map of regions of skin affected with skin disease.

In other embodiments of the fiber optic comb, some prongs can be dedicated to delivering therapeutic radiation and other prongs can be dedicated to delivering and receiving diagnostic radiation. Furthermore, in other arrangements, certain prongs can be configured to received diagnostic radiation, e.g., fluorescence or diffuse reflectance, caused by diagnostic radiation delivered to the skin by a different prong. Such an arrangement permits diagnostic detection from different depths within the tissue. This is because the volume of tissue irradiated by each prong delivering diagnostic radiation and the volume of tissue probed by each prong detecting diagnostic signal radiation extend radially outward from the respective prongs. Thus, the depth of the overlapping emission and detection volumes increases with the separation of the prongs emitting the diagnostic radiation and detecting diagnostic signal radiation.

In other embodiments of manual devices such as the fiber optic pen and comb, the illumination source can irradiate the patient's skin directly rather than being delivered through the manual device. Even in such cases, the manual device receives diagnostic signal radiation caused by directly irradiating the patient's skin with the illumination source. Also, in alternative embodiments, the manual device can include the illumination source and detector as part of the manually operated instrument.

OTHER EMBODIMENTS

It is to be understood that while the invention has been described in conjunction with the detailed description thereof, that the foregoing description is intended to illustrate and not limit the scope of the invention, which is defined by the scope of the appended claims. For example, in addition to psoriasis, the automated radiation treatment systems and methods can also be used to treat other inflammatory, proliferative skin disorders that respond to UV radiation, such as mycosis fungoides, eczema, and lichen planus. Tryptophan fluorescence and diffuse reflectance are also suitable diagnostics for these disorders.

Other aspects, advantages, and modifications are within the scope of the following claims.

What is claimed is:

1. A method for treating a proliferative skin disorder in a patient, the method comprising:
   performing at least two different optical diagnostics on a selected area of the patient's skin, wherein each diagnostic independently provides a positive indication when the skin disorder is present in the selected area;
   determining from the optical diagnostics whether the selected area is affected by the skin disorder based on whether each diagnostic provides the positive indication; and
   if the selected area is determined to be affected by the skin disorder, delivering an effective dose of phototherapeutic radiation to the selected area.

2. The method of claim 1, wherein the method is performed in an automated manner.

3. The method of claim 1, wherein the disorder is psoriasis.

4. The method of claim 1, wherein the selected area is less than about 1 $cm^2$.

5. The method of claim 1, wherein the phototherapeutic radiation is ultraviolet radiation having a wavelength of about 290 nm to 330 nm, and wherein the effective dose is in the range of about 0.02 $J/cm^2$ to 1 $J/cm^2$.

6. The method of claim 1, wherein the effective dose is greater than about two minimal erythema doses.

7. The method of claim 1, wherein the effective dose is greater than about three minimal erythema doses.

8. The method of claim 1, wherein the effective dose is greater than about ten minimal erythema doses.

9. The method of claim 1, wherein one of the optical diagnostics relates to diffuse reflectance.

10. The method of claim 1, wherein the at least two different optical diagnostics comprise diffuse reflectance and fluorescence.

11. The method of claim 1, wherein the at least two different optical diagnostics measure different physiological properties of the skin disorder.

12. The method of claim 1, wherein the phototherapeutic radiation is ultraviolet radiation.

13. The method of claim 1, wherein the phototherapeutic radiation is delivered by a laser.

14. The method of claim 13, wherein the laser is a xenon chloride excimer laser.

15. The method of claim 1, wherein one of the optical diagnostics relates to fluorescence.

16. The method of claim 15, wherein the performing step comprises delivering a diagnostic dose of radiation from a source, wherein the diagnostic dose is sufficient to excite the fluorescence from the selected area but is not an effective dose of phototherapeutic radiation, and wherein the delivering step comprises delivering an effective phototherapeutic dose of radiation from the source by increasing fluence of the source.

17. The method of claim 1, further comprising:
   constructing a digital map of areas of the patient's skin affected by the skin disorder by repeating the performing and determining steps for additional selected areas; and
   delivering effective doses of phototherapeutic radiation to at least one of the affected areas indicated on the map.

18. The method of claim 17, wherein the effective doses of phototherapeutic radiation are delivered to each of the affected areas indicated on the map.

19. The method of claim 17, further comprising:
   performing an additional optical diagnostic on each of the areas indicated on the map to confirm that these areas are affected and designating the confirmed areas as treatment areas; and
   delivering an effective dose of phototherapeutic radiation to at least one of the treatment areas.

20. The method of claim 17, wherein the constructing step is completed before the delivering step.

* * * * *